(12) United States Patent
Kim et al.

(10) Patent No.: US 8,697,415 B2
(45) Date of Patent: Apr. 15, 2014

(54) DEACETYLATION HYDROLASE OF HYALURONIC ACID, HYALURONIC ACID DEACETYLATED BY SAME AND DERIVATIVE THEREOF

(75) Inventors: Chun-Ho Kim, Seoul (KR); Jong-Il Kim, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 13/703,619

(22) PCT Filed: Jun. 10, 2011

(86) PCT No.: PCT/KR2011/004290
§ 371 (c)(1),
(2), (4) Date: Dec. 11, 2012

(87) PCT Pub. No.: WO2011/155800
PCT Pub. Date: Dec. 15, 2011

(65) Prior Publication Data
US 2013/0085187 A1    Apr. 4, 2013

(30) Foreign Application Priority Data

Jun. 11, 2010 (KR) ........................ 10-2010-0055562

(51) Int. Cl.
*C12N 9/78* (2006.01)
(52) U.S. Cl.
USPC .......................................... 435/227; 514/777
(58) Field of Classification Search
USPC .................................. 435/227, 85
See application file for complete search history.

(56) References Cited

FOREIGN PATENT DOCUMENTS

WO        94/13815 A1    6/1994

OTHER PUBLICATIONS

Prestwich, et al., "Chemically-Modified HA for Therapy and Regenerative Medicine", Current Pharmaceutical Biotechnology, 2008, 9(4), pp. 242-245.
Balazs, et al., "Hyaluronic acid and replacement of vitreous and aqueous humor", Mod. Probl. Ophthalmol., 1972, 10, pp. 3-21.
Isdale, et al., "Intra-articular hyaluronate (Healon): A dose-ranging study in rheumatoid arthritis and osteoarthritis", J. Drug Dev., 1991, 4, pp. 93-99.
Kawabata, et al., "Clinical evaluations of SLM-10 (sodium hyaluronate injection) in patients with Osteoarthritis of the Knee: A Multi-Center Comparative Trial with ARTZ as Control Drug", Japan Pharmacol Ther), 1993, vol. 21, pp. 257-283.
Fraser, et al., "Hyaluronan: its nature, distribution, functions", and turnover, J. Intern. Med., 1997, 242(1), pp. 27-33.
Laurent, et al., "Hyaluronan", The FASEB Journal, 1992, vol. 6, pp. 2397-2404.
Laurent, et al., "Turnover of hyaluronan in the tissues", Advanced Drug Delivery Reviews, 1991, vol. 7, pp. 237-256.
Soh, "Hyaluronic acid: properties and application", Polymer(Korea), 1998, in 15 pages.
Crescenzi, et al., "New cross-linked and sulfated derivatives of partially deacetylated hyaluronan: Synthesis and preliminary characterization", Biopolymers, 2002, vol. 64, pp. 86-94.
Oerther, et al., "High Interaction Alginate-Hyaluronate Associations by Hyaluronate Deacetylation for the Preparation of Efficient Biomaterials", Biopolymer, 2000, vol. 54, pp. 273-281.
Oh, et al., "Control of the molecular degradation of hyaluronic acid hydrogels for tissue augmentation", J Biomed Mater Res A., 2008, 86(3), pp. 685-693.
Hahn, et al., "Synthesis and degradation test of hyaluronic acid hydrogels", Int J Biol Macromol., 2007, 40(4), pp. 374-380.
Crescenzi, et al., "New hyaluronan chemical derivatives. Ragioselectively C(6) oxidized products", Macromolecules, 2001, vol. 34, pp. 6367-6372.
Araki, et al., "A pathway of Chitosan Formation in *Mucor* rouxii", Eur. J. Biochem., 1975, 55, pp. 71-78.
Martinou, et al., "Chitin deacetylation by enzymatic means: monitoring of deacetylation process", Carbohyd. Res., 1995, 273, pp. 235-242.
Ito, et al., "Anti-inflammatory function of an in situ cross-linkable conjugate hydrogel of hyaluronic acid and dexamethasone", Biomaterials 28, 2007, pp. 1778-1786.
Longas, et al., "Hyaluronic Acid N-Deacetylase Assay in Whole Skin", Biomacromolecules, 2003, vol. 4, No. 1, pp. 189-192.
GenBank Accession No. XM_654364: *Aspergillus nidulans* FGSC A4 hypothetical protein AN1852.2 partial mRNA, 2004.
Tsigos, et al., "Chitin deacetylases: new, versatile tools in biotechnology", Trends Biotchnol. 2000, vol. 18, No. 7, pp. 305-312.
Zhao, et al., "Chitin Deacetylases: Properties and Applications", Marine Drugs. Jan. 14, 2010, vol. 8, pp. 24-26.

*Primary Examiner* — Tekchand Saidha
*Assistant Examiner* — Rama P Ramanujam
(74) *Attorney, Agent, or Firm* — Knobbe, Martens, Olson & Bear, LLP (57) ABSTRACT

The present disclosure relates to a deacetylation hydrolase of a hyaluronic acid a hyaluronic acid deacetylated by same and a derivative thereof. The deacetylated hyaluronic acid and the derivative thereof have the following characteristic: a delayed initial decomposition rate on a living body; minimized decrease of molecular weight and viscosity; accelerated gelation due to a lower gelation temperature than the gelation temperature for a non-deacetylated hyaluronic acid; and an hMSC survival rate that is hardly affected by increased concentration of the deacetylated hyaluronic acid and the derivative thereof in a culture medium. As a result, the deacetylated hyaluronic acid and the derivative thereof can be useful as a bioingredient such a delivery system for a cell, gene, drug, and the like, or a support for tissue engineering, etc.

11 Claims, 9 Drawing Sheets

(a) 3days (b) 6days

SEQUENCE LISTING

<160> NUMBER OF SEQ ID NOS: 1

<210> SEQ ID NO 1
<211> LENGTH: 750
<212> TYPE: DNA
<213> ORGANISM: Artificial Sequence
<220> FEATURE:
<223> OTHER INFORMATION: deacetylation hydrolase of hyaluronic acid
      isolated from Aspergillus nidulans

<400> SEQUENCE: 1

```
atgctgtttc ctaatgtgcc gggtgtggca tctcttctct cactcttcgc cgcaaccctc    60
atcctaaaca ctcaagccct agccatcaat acaatagcaa acctcacaga ccgacaaccg   120
cgtgtttcct acggtctata cattcaccat tgctacgttc ctggagtggt agccctaacc   180
ttcgatgacg gaccctacat ttacacagaa gaactcctcg acatactcgc gcagtacggc   240
gccaaagcga ccttctttgt gaatggccac aatctagctg gcaacgaatg gctcatccag   300
cgtgttgtaa atgaaggcca ccagctagca tcgcacacat ggggccatac cgatcttact   360
gttctcagct atgatcaaat cgtcgaccaa atgacccgac tcgagtctgc ctttgtagca   420
tccgtcgggg tagtccctac ctacatgagg ccaccgtacc tcgccgccaa tgactatgtt   480
ctgggcgtca tggctgaact cggctaccat gtcattggtg ctagtgtcga taccaaggac   540
tatgagaacg atcatcctga tctgattgga cgtagtgtgg ccaagtttaa ccaggagcta   600
gatcagggag gaacgatcgt cttgtcgcat gacattcacg aacagactgt gcgaactctg   660
acacacatca tgctggagga agtgtacgaa cgagggttgc agcctacaac tgtcggaggt   720
tgtcttggtg acgacgcatg gtaccgttag                                    750
```

DEACETYLATION HYDROLASE OF HYALURONIC ACID, HYALURONIC ACID DEACETYLATED BY SAME AND DERIVATIVE THEREOF

TECHNICAL FIELD

The present invention relates to a deacetylation hydrolase of hyaluronic acid, and a deacetylated hyaluronic acid or a derivative thereof, prepared using the deacetylation hydrolase.

BACKGROUND ART

Hyaluronic acid belongs to glycosaminoglycans (GAGs), like heparan sulfate, chondroitin sulfate, dermatan sulfate, and herapin, and is a polyanionic natural linear polymer of repeating units, each composed of N-acetyl-D-glucosamine and D-glucuronic acid. Hyaluronic acid is found in the eyes, the placenta, the synovial fluid lubricant of body joints, the skin, and the comb of chicken and ranges in molecular weight from $10^3$ to $10^7$ Daltons depending on the in vivo site at which it is found. In addition, hyaluronic acid is a main component of the extracellular matrix plays an important role as a scaffold in all layers of the skin including the epidermis and dermis. Hyaluronic acid is also found in the synovial fluid, the umbilical cord, and the blood of all higher animals, and almost 50% of the body's hyaluronic acid is located in the skin, the respiratory tract, and the intestinal tract. It is unique among glycosaminoglycans in that it is nonsulfated. Due to its abundant negative charges, HA can bind cations and absorb large amounts of water, acting as an osmotic buffer in the native ECM and forming hydrogel. Hence, hyaluronic acid may be an excellent alternative to other components of ECM, and thanks to its excellent water retention, hyaluronic acid provides the homeostasis of ECM hydration for tissues and joints and is responsible for resistance to the compression by physical force. In addition, hyaluronic acid is involved in permeability regulation between tissues, functions to induce a lubricant effect on friction in the joints, and acts as a carrier for providing nutrients to or removing wastes from avascular regions in the joint.

Taking advantage of its high water absorptivity and viscosity, accordingly, the naturally occurring hyaluronic acid itself or its derivatives (Glenn D. Prestwich, Jing-wen Kuo, Chemically-Modified HA for Therapy and Regenerative Medicine, Current Pharmaceutical Biotechnology, 9(4), 242-245 (2008)) have been applied to cosmetics or medically to the eyes (E. A. Balazs, M. I. Freeman, R. Kloti, G. Meyer-Schwickerath, F. Regnault, and D. B. Sweeney, "Hyaluronic acid and replacement of vitreous and aqueous humor", *Mod. Probl. Ophthalmol.*, 10, 3~21 (1972)). In addition, hyaluronic acid finds various applications in the field of tissue regeneration and engineering, including the regeneration of cartilage and bones (A. H. Isdale, L. D. Hordon, H. A. Bird, and V. Wright, "Intra-articular hyaluronate (Healon): A dose-ranging study in rheumatoid arthritis and osteoarthritis", *J. Drug Dev.*, 4, 93~99 (1991). M. Kawabata, M. Igarashi, R. Mikami, S. Ninomiya, and H. Oda, "Clinical evaluations of SLM-10 (sodium hyaluronate injection) in patients with osteoarthritis of the knee", *Yakuri to Chiryo*, 21, 257~283 (1993)), the reconstruction of the skin and soft tissues, and the resurfacing and plastic surgery of repressed tissues, for example, by directly injecting hyaluronic gel into the body.

Despite its useful applicability as a medical biomaterial, hyaluronic acid is limited in many of its uses because of its short half life in vivo. In fact, hyaluronic acid is too easily degraded in vivo, with a shorter half life than collagen. In bone and cartilage where lymph fluid is not secreted, it is probable that hyaluronic acid turnover occurs by metabolic degradation in situ concurrently with that of collagen and proteoglycans. In skin and joints, 20~30% of hyaluronic acid is probably turned over by local metabolism, and the rest is removed by the lymphatic pathway. The tissue half-life of hyaluronic acid ranges from half a day to 2 or 3 days (J. R. E. Fraser, T. C. Laurent, and U. B. G. Laurent, Hyaluronan: its nature, distribution, functions, and turnover, J. Intern. Med., 242(1), 27-33 (1997)). Particularly, when used as an implant in a normal joint, hyaluronic acid is reported to have a half life of less than one day (T. C. Laurent, and J. R. E. Fraser, Hyaluronan, FASEB J., 6, 2397-2404 (1992)). The half life of hyaluronic acid is extended to 70 days in the eye where hyaluronic acid is not combined with other glycosaminoglycans (U. B. G. Laurent, and R. K. Reed, Turnover of hyaluronan in the tissue, Adv. Drug Delivery Rev., 7, 237-56 (1991)).

In spite of its great potential as a medical biomaterial, hyaluronic acid is currently limitedly used because of its fast degradability and short half life in vivo as well as the low mechanical properties of the natural polymer itself. For use in plastic surgery, hyaluronic acid gel must retain a desired mechanical strength for a long period of time in the body, and is usually prepared from hyaluronic acid with an ultrahigh molecular weight of 2,000~3,000 kDa because it has a short half life.

Further, hyaluronic acid is required to be chemically modified and developed into derivatives that retain the hyaluronic acid structure but do not undergo the rapid degradation in vivo, so that they can be used as biomaterials for various clinical purposes. Many chemical modification attempts have been made on hyaluronic acid. For example, hyaluronic acid is crosslinked, is prepared into alkyl and benzylester derivatives, or modified with a coupling agent. Reviewing the research reports known thus far, hyaluronic acid derivatives developed by chemical modifications have proven suitable as medical polymers having mechanical and chemical properties for use in target tissues, organs and drug delivery systems. Some of them were shown to retain the hyaluronic acid's intrinsic biological functions in light of pharmaceutical functions. However, it is difficult to synthesize hyaluronic acid derivatives with a molecular weight of $1.5 \times 10^6$ Daltons or greater by chemical modification because such high-molecular weight polymers are likely to undergo intermolecular entanglement (Y. S. Soh, "Hyaluronic acid: properties and application", Polymer (Korea), 12, (1988)).

Various solutions to the above-mentioned problems have been suggested. For example, a hyaluronic acid with a lower molecular weight may be prepared, or after the N-acetyl-D-glucosamine moiety is deacetylated with hydrazine, the resulting hyaluronic acid with an organic amine group may be chemically modified (V. Crescenzi, A. Francescangeli, D. Renier, D. Bellini, New cross-linked and sulfated derivatives of partially deacetylated hyaluronan: Synthesis and preliminary characterization, Biopolymers, Vol. 64, 86-94 (2002). S. Oerther, A-C Maurin, E. Payan, P. Hubert, F. Lapicque, N. Presle, J. Dexheimer, P. Netter, and F. Lapicque, High Interaction alginate-hyaluronate associations by hyaluronate deacetylation for the preparation of efficient biomaterials, Biopolymer, 54, 273-281 (2000)). In addition, the carboxyl group at position 6 of the beta-glucuronic acid, known as the target site of hyaluronidase, may be chemically substituted to prepare water-insoluble hyaluronic acid gels (Oh E J, Kang S W, Kim B S, Jiang G, Cho I H, Hahn S K., Control of the molecular degradation of hyaluronic acid hydrogels for tissue augmentation. J Biomed Mater Res A., 86(3):685-93 (2008) Hahn S K, Park J K, Tomimatsu T, Shimoboji T., Synthesis and degradation test of hyaluronic acid hydrogels. Int J Biol Macromol., 40(4), 374-80 (2007).). Further, chemical modifications may be made not only on the alcohol (—OH) groups within the repeating units, but also by disrupting the sugar ring structures, and a physical modification using the negatively charge on the carboxylic acid group has also been reported (V. Crescenzi, A. Francescangeli, D. Renier, D. Bellini, New hyaluronan chemical derivatives. Regioselectively C (6) oxidized products, Macromolecules, 34, 6367-6372 (2001)). However, chemical deacetylation, and chemical modification using a coupling agent, produces hyaluronic acid with a significantly reduced molecular weight, which results in weakening of the intrinsic mechanical property of hyaluronic acid (S. Oerther, A-C Maurin, E. Payan, P. Hubert, F. Lapicque, N. Presle, J. Dexheimer, P. Netter, and F. Lapicque, High Interaction alginate-hyaluronate associations by hyaluronate deacetylation for the preparation of efficient biomaterials, Biopolymer, 54, 273-281 (2000)). Furthermore, the deacetylation or modification may cause the separation of multivalent metals used for ionic crosslinking and the dissociation of introduced functional groups, which, together with degraded hyaluronic acid, are highly apt to exert cytotoxicity. In addition, hyaluronic acid with reduced mechanical strength is greatly limited in its use as a biomaterial in medical and industrial fields, and cannot be formulated into various types of biomaterial. Particularly when hydrogels, sheets, film, beads, or nanofibers are applied as tissue engineering scaffolds to regenerative medicine, their strengths and morphologies must be maintained until surrounding cells are introduced into the scaffolds so as to rapidly construct tissues. Otherwise, their morphologies may readily collapse, with a significant reduction in efficacy and engraftment to surrounding tissues. Therefore, in order to maintain the framework necessary of hyaluronic acid to act as a tissue engineering scaffold as well as serving as a carrier of cells, proteins, metals and drugs, and as a coating agent, the biodegradability of hyaluronic acid and its molecular weight must be possible to regulate.

On the other hand, deacetylation hydrolase of the N-acetyl-D-glucosamine moiety has been studied, mainly with chitin deacetylation hydrolase (CDA: E, C, 3.5.1.41), which catalyzes the conversion of chitin into chitosan. In 1936, Watanabe reported the likelihood of the existence of N-acetyl-D-glucosamine deacetylase in animal tissues, and S. Roseman first isolated the enzyme from an extract of *E. coli* strain K-12 in 1957. Subsequently, chitin deacetylation hydrolase has successfully been isolated from an extract of *Mucor rouxii*, and an extract of *Bacillus cereus*; fungi, such as *Colletotrichum lindemuthianum, Colletotrichum lagenarium,* and *Rhizopus stolonifer*; insect species; crustacea; and *Encephalitozoon cuniculi*, which is a protozoa. In addition, research results of the isolation and purification of chitin deacetylation hydrolase from *Mucor rouxii, Absidia coerulea,* and *Aspergillus nidulans* were reported. Isolation of cobalt-activated chitin deacetylation hydrolase (Cda2P) from *Gongronella butleri* and *Saccharomyces cerevisiae*, and chitin deacetylation hydroloase from *Encephalitozoon cuniculi, Metarhizium anisopliae*, and culture media of *E. coli* and *Rhizopus oryzae* was successful. In recent years, there have been reports on the isolation of chitin deacetylation hydrolase from *Scopulariopsis brevicaulis, Mortierella* sp. DY-52, *Rhizopus circinans*, and *Vibrio cholera*, but purification results thereof have not yet established.

In addition, since the finding that there is structural similarity between fungal chitin deacetylases and rhizobial nodulation proteins (NodB proteins), sequences of chitin deacetylases from fungi such as *Mucor rouxii, Colletotrichum lindemuthianum, Saccharomyces cerevisiae, Gongronella butleri,* and *Rhizopus nigricans* have been examined, but not yet reported.

As illustrated above, research into deacetylation hydrolase of polysaccharides has been centered around chitin deacetylation hydrolases, which, while not reactive to the monosaccharide N-acetyl-D-glucosamine, are able to act catalytically on a series of consecutive N-acetyl-D-glucosamine residues. Such chitin deacetylation hydrolase do not show enzymatic activity on the peptidoglycan N-acetylated heparin, and N-acetyl-galactosamine (Araki, Y. & Ito, E. (1975). A pathway of chitosan formation in *Mucor rouxii*, Eur. J. Biochem., 55, 71-78 (1975)), and cannot catalyze the deacetylation of the N-acetyl-D-glycosamine moiety of hyaluronic acid (Martinou A, Kafetzopoulos D, Bouriotis V., Chitin deacetylation by enzymatic means: monitoring of deacetylation process, Carbohyd. Res., 273, 235-242 (1995)). Like this, the chitin deacetylation hydrolase have been reported to have no enzymatic activity except for on N-acetyl-D-glucosamines of chitin and chitosan. That is, nowhere has a deacetylase selective for the acetyl group of the N-acetyl-D-glucosamine moiety of hyaluronic acid been reported in any previous documents.

There is therefore a need for research and development of a deacetylation hydrolase that can selectively deacetylate the N-acetyl-D-glucosamine moiety of hyaluronic acid.

DISCLOSURE

Technical Problem

The present inventors have researched a deacetylation hydrolase that is selective for the acetyl group of the N-acetyl-D-glucosamine of hyaluronic acid, succeeded in isolating and purifying a hyaluronic acid deacetylase from a microbe, and found that the deacetylase was useful in preparing deacetylated hyaluronic acids and derivatives thereof and that the deacetylated hyaluronic acids and derivatives thereof underwent degradation at a lower rate in vivo, with the minimal reduction in molecular weight and viscosity, had a lower gel point, thereby accelerating gelation, and had no influences on the cell viability of hMSCs, which leads to the present invention.

Technical Solution

It is an object of the present invention to provide a deacetylation hydrolase of hyaluronic acid, isolated and purified from a microbe, which is capable of catalyzing the selective hydrolysis of the acetyl group on the N-acetyl-D-glycosamine moiety of hyaluronic acid.

It is another object of the present invention to provide a deacetylated hyaluronic acid or a derivative thereof, prepared using the deacetylation hydrolase of hyaluronic acid of the present invention.

Advantageous Effects

The deacetylated hyaluronic acid and its derivatives in accordance with the present invention are less apt to undergo degradation for the initial time period after implantation into the body, and show significantly low reduction in molecular weight and viscosity, and a gel point lower than that of undeacetylated hyaluronic acid, thus accelerating gelatins. Also, they have almost no negative influences on the cell viability of hMSCs even at high concentrations. Consequently, the deacetylated hyaluronic acids and derivatives thereof in accordance with the present invention can be applied as a biomaterial such as a carrier for cells, genes, and drugs, and a tissue engineering scaffold.

BEST MODE

In accordance with an aspect thereof, the present invention addresses deacetylation hydrolase of a hyaluronic acid that catalyzes the selective hydrolysis of the acetyl group on the N-acetyl-D-glucosamine of hyaluronic acid.

In accordance with another aspect thereof, the present invention addresses a hyaluronic acid deacetylated by the deacetylation hydrolase, and a derivative thereof.

Below, a detailed description will be given of the present invention.

The deacetylation hydrolase of the present invention is isolated and purified from a microbe, and acts to selectively hydrolyze an acetyl group from the N-acetyl-D-glucosamine moiety of hyaluronic acid.

Examples of the microbe include *Aspergillus nidulans*, *Scopulariopsis brevicaulis*, *Mucor rouxii*, *Bacillus cereus*, *Colletotrichum lagenarium*, *Rhizopus stolonifer*, *Absidia coerulea*, *Gongronella butleri*, *Saccharomyces cerevisiae*, *Encephalitozoon cuniculi*, *Metarhizium anisopliae*, *Streptococus pneumoniae*, *Mortierella* sp. DY-52, *Rhizopus circinans*, and *Vibrio cholerae*, but are not limited thereto. In one embodiment, the deacetylation hydrolase of the present invention was isolated and purified from *Aspergillus nidulans* and *Scopulariopsis brevicaulis*, and the nucleotide sequence of the deacetylation hydrolase from *Aspergillus nidulans* was analyzed and is represented by SEQ ID NO: 1.

In addition, the present invention pertains to a deacetylated hyaluronic acid prepared using the deacetylation hydrolase of hyaluronic acid, and a derivative thereof. In detail, hyaluronic acid or a derivative thereof is dissolved in a buffer, pH 3.0~9.0, or distilled water, and incubated with a deacetylation hydrolase of hyaluronic acid at 10~70° C., and preferably at 30~60° C. for 0.001~24 hrs, and more preferably for 1~10 hrs, and most preferably for 3~6 hrs, followed by adding ethanol to the reaction mixture to precipitate a deacetylated hyaluronic acid or a derivative thereof. In this context, the amount of ethanol is 2~10 times and preferably about 4~7 times the weight of the reaction mixture. Subsequently, the precipitate of deacetylated hyaluronic acid or a derivative thereof is washed with ethanol, dissolved in distilled water, and dialyzed against distilled water before lyophilization.

The deacetylation hydrolase of the present invention can more effectively remove acetyl groups from hyaluronic acid than can chemical methods, as proven by the higher degree of deacetylation in the enzymatically deacetylated hyaluronic acid than chemically deacetylated hyaluronic acid.

It is found that the initial in vivo degradation of the deacetylated hyaluronic acid of the present invention by hyaluronidase is delayed, with the minimal reduction in molecular weight and viscosity, so that the deacetylated hyaluronic acid with a high molecular weight and a high viscosity can be prepared.

In addition, the gelling point of the deacetylated hyaluronic acid of the present invention is lower than that of non-deacetylated, that is, intact hyaluronic acid, indicating that the gelling of the deacetylated hyaluronic acid is accelerated by electrostatic interaction between anionic beta-glycidylphosphate and the cationic free amine group of the deacetylated hyaluronic acid.

No significant differences in the morphology of hMSC were observed depending on the concentration of the deacetylated hyaluronic acid of the present invention, and the viability of hMSC was basically unaffected, with an increase in the concentration of the deacetylated hyaluronic acid in culture media.

As described hitherto, the deacetylated hyaluronic acid and derivatives thereof in accordance with the present invention are degraded at a delayed rate in vivo, with a minimal reduction in molecular weight and viscosity, are more apt to gel with a gel point lower than that of un-deacetylated hyaluronic acid, and have almost no influence on the cell viability of hMSC, although its concentration increases in the cell culture medium. Therefore, the deacetylated hyaluronic acid and its derivatives in accordance with the present invention can be useful as biomaterials applicable to a carrier of cells, genes, and drugs, or a tissue engineering scaffold.

A better understanding of the present invention may be obtained through the following examples which are set forth to illustrate, but are not to be construed as limiting the present invention.

EXAMPLE 1

Isolation and Purification of Hyaluronic Acid Deacetylase from *Aspergillus nidulans*

1. Culture of *Aspergillus nidulans*

*Aspergillus nidulans* was initially cultured at 5~40° C. for 4~2,400 hrs in broth [(glucose 5 g, yeast extract 2 g, peptone 5 g, NaCl 5 g) or (1% glucose, 0.15% yeast extract, 0.15% casein hydrolysate, 1× vitamin solution, 1× minimal salt solution, 0.5% chitin) in a total volume of 1 L] or a plate [3% sucrose, 0.2% $NaNO_3$, 1% $K_2HPO_4$, 0.05% KCl, 0.05% $MgSO_4$], and then at 5~40° C. for 4~200 hrs in broth [($NaNO_3$ 2 g, $K_2HPO_4$ 1 g, KCl 0.5 g, $MgSO_4$ 0.5 g, peptone 1 g, chitin 0-10 g) or (1% glucose, 0.15% yeast extract, 0.15% casein hydrolysate, 1× vitamin solution, 1× minimal salt solution, 0.5% chitin)] or a plate [3% sucrose, 0.2% $NaNO_3$, 1% $K_2HPO_4$, 0.05% KCl, 0.05% $MgSO_4$] with shaking at 1~1,000 rpm. The vitamin solution contained 15.2% $NaNO_3$, 2.6% $MgSO_4$, 15.2% $K_2HPO_4$, 2.6% KCl, 0.04% $ZnCl_2$, 0.4% $(NH_4)_2Mo_7O_{24}$, 0.001% $MnCl_2$, 0.03% $CuSO_4$, and 0.001% $FeSO_4$, and the minimal salt solution contained riboflavin 50 mg, p-aminobenzoic acid 250 mg, pyridoxine-HCl 250 mg, biotin 2 mg, ascorbic acid 250 mg, folic acid 250 mg, thiamine 250 mg, and nicotinic acid 50 mg per 500 mL.

For intracellular enzyme proteins, the fungal mycelia were disrupted by ultrasonication, followed by centrifugation at 1,000~100,000 ×g for 1~500 min. The supernatant was treated for 0~48 hrs with a gradient of 0~100% ammonium sulfate. After centrifugation at, 1,000~100,000 ×g for 0~500 min, the supernatant was treated for 0.1~48 hrs with a gradient of 0~100% ammonium sulfate. Centrifugation at 1,000~50,000 ×g for 1~500 min afforded the enzyme as a precipitate. For extracellular enzyme proteins, 6 L of the cell culture was subjected to be saturated with 0~100% ammonium sulfate (Sigma Chemical Co., St. Louis, Mo., USA). After centrifugation at 1,000~100,000 ×g for 0~500 min, the supernatant was saturated with 0-100% ammonium sulfate. Then, centrifugation at 1,000~100,000 ×g for 0~500 min afforded the enzyme as a precipitate.

The *Aspergillus nidulans* precipitates were harvested and suspended in Tris-HCl buffer (pH 7.5), and the suspension was dialyzed overnight against 0~100% ammonium sulfate (50 mM Tris-HCl, pH 7.5).

2. Enzymatic Deacetylation Activity of Precipitate from *Aspergillus nidulans* Culture According to precipitation with Ammonium Sulfate The enzymatic deacetylation activity of the precipitates from *Aspergillus nidulans* cultures according to the concentrations of ammonium sulfate was analyzed by determining the level of acetate ions produced upon the enzymatic hydrolysis of penta-N-acetylchitohexadose. In this regard, the degree of deacetylation was determined using a coupled enzyme assay by which the level of free acetate ions separated from the sugar was measured.

In an acetic acid kit (ENZYTEC™), as illustrated in the following reaction scheme, acetate ions are released by the enzymatic action of deacetylase and sequentially reacted in the presence of ACS, CS and MDH, with the concomitant stoichiometric production of NADH. NADH was quantitatively analyzed by absorbance at 340 nm with an extinction coefficient $e_{340}$=6.31 $mM^{-1}$ $cm^{-1}$.

For control, 330 μL of TEA (triethanolamine) buffer, 67 μL of an ATP/CoA/NAD solution, 4 μL of an MDH/CS solution, 7 μL of an ACS solution, all contained in the acetic acid kit, were sequentially added into a 1.5 mL e-tube in that order, and the tube was filled with distilled water to form a total volume of 1 mL. After incubation at 25° C. for 30 min, the reaction was transferred into 96-well plates, and absorbance at 340 nm was read on a microplate reader (SpectraMax® M2, Molecular Devices, USA).

When measured with penta-N-acetylchitohexadose serving as a substrate, the deacetylation activity of the precipitates from *Aspergillus nidulans* cultures according to the concentration of ammonium sulfate is summarized in Table 1, below.

TABLE 1

| | Conc. of Ammonium Sulfate (%) | | | | |
|---|---|---|---|---|---|
| | 0% | 1~30% | 31~50% | 51~70% | 71~100% |
| Conc. of Acetate Produced ($A_{340}$) | 0.285 | 0.852 | 0.711 | 0.321 | 0.314 |

Figure 1:
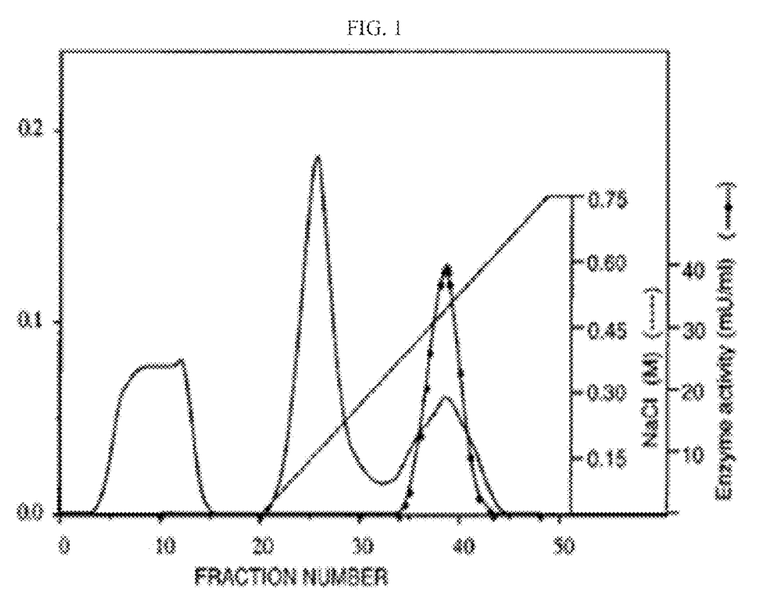
FIG. 1 is a chromatogram the activity of the hyaluronic acid deacetylase, isolated and purified from *Aspergillus nidulans*, on the chitin oligomer penta-N-acetylchitohexadose.

As is understood from the data of FIG. 1, excellent deacetylation activity of the precipitate from *Aspergillus nidulans* cultures was detected in fractions with an ammonium sulfate concentration of 1~50%. Thus, hyaluronic acid deacetylase was isolated from the precipitates from the *Aspergillus nidulans* cultures saturated with 1~50% ammonium sulfate.

3. Isolation and Purification of Hyaluronic Acid Deacetylase from *Aspergillus nidulans* Culture Precipitates from *Aspergillus nidulans* cultures saturated with 1~50% ammonium sulfate were fractionated through a Sephadex G-100 column (Sigma), or a phenyl sepharose CL-4B column combined with a Q-sepharose column, all kept at 4° C. in a refrigeration chamber. A sample was loaded into a phenyl-sepharose CL-4B (2.5×6 cm, Sigma Chemical Co., St. Louis, Mo., USA) column for hydrophobic interaction, and eluted with 0~1.0 M ammonium sulfate. The elute was then fractioned through an anion exchange chromatography on Q-sepharose column (2.5×4 cm, Sigma Chemical Co., St. Louis, Mo., USA). The 0.01~5M fractions, which were highly active, were dissolved to form a $(NH_4)_2SO_4$ 80% saturated solution, concentrated, and dialyzed overnight against 50 mM Tris-HCl, pH 7.5 to isolate hyaluronic acid deacetylase. Alternatively, protein precipitates from 1~50% ammonium sulfate saturated solutions were dissolved in 50 mM Tris-HCl, pH 7.5 and loaded into a Sephadex G-100 column (Sigma) (1.6×60 cm). Elution was performed using Tris-HCl 50 mM, pH 7.5, as an eluent. Of the fractions harvested, the hyaluronic acid deacetylase fraction was treated with 0.1~48 hrs with 0~100% ammonium sulfate. Centrifugation at 1,000~100,000 ×g for 1~500 min and concentration afforded pure hyaluronic acid deacetylase. This isolated and purified hyaluronic acid deacetylase was analyzed for enzymatic activity using the chitin oligomer penta-N-acetylchitohexaose.

The result is given in FIG. 1.

As shown in FIG. 1, hyaluronic acid deacetylase activity was detected in 25 mM Tris-HCl (pH 7.5) containing 0.5M NaCl.

4. Identification of Hyaluronic Acid Deacetylase (SDS-PAGE)

The hyaluronic acid deacetylase isolated and purified from *Aspergillus nidulans* was identified using SDS-polyacrylamide gel electrophoresis (SDS-PAGE). In this regard, 10% denatured polyacrylamide gel was prepared, and the purified hyaluronic acid deacetylase was loaded, together with a marker (SeeBlue Plus2 Prestained Standard, invitrogen, Carlsbad, Calif.), into the gel, and run at 120 V. Following electrophoresis, the gel was stained for 30 min in Coomassie Brilliant Blue R-250, and immersed in a destaining solution (50% methanol, 10% acetic acid).

Figure 2:
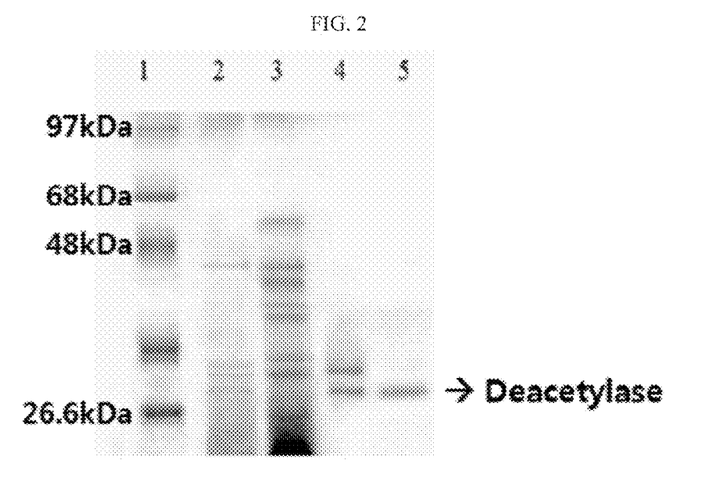
FIG. 2 is a photograph showing the isolation and purification of hyaluronic acid deacetylase as analyzed by SDS-polyacrylamide gel electrophoresis (SDS-PAGE) [lane 1: maker (standard molecular weight), lane 2: 30% ammonium sulfate fraction, lane 3: Q-sepharose fraction (unbound), lane 4: phenyl-sepharose fraction, lane 5: sephacryl fraction].

The result is given in FIG. 2.

As can be seen in FIG. 2, the hyaluronic acid deacetylase isolated and purified from *Aspergillus nidulans* was observed to have a molecular weight of about 28 kDa.

5. Nucleotide Sequence of Gene for Hyaluronic Acid Deacetylase

The hyaluronic acid deacetylase was examined for amino acid sequence using an Edman degradation method. The amino acid sequence that was thus obtained from a part of the enzyme protein was used to search for the full-length amino acid sequence of the hyaluronic acid deacetylase from a well-known database. In addition, the nucleotide sequence of the hyaluronic acid deacetylase was inferred from the full-length amino acid sequence, and is represented by SEQ ID NO: 1.

EXAMPLE 2

Isolation and Purification of Hyaluronic Acid Deacetylase from Scopulariopsis Brevicaulis Hyaluronic acid deacetylase of *Scopulariopsis brevicaulis* was isolated and purified in the same manner as in Example 1, with the exception that *Scopulariopsis brevicaulis* (ATCC 36009) was used instead of *Aspergillus nidulans*.

The hyaluronic acid deacetylase isolated from Scopulariopsis brevicaulis was examined for mean molecular weight by aqueous chromatography using HPLC Waters M515 and Waters 486 detector with Annexin V and BioBasic SEC-120 (3007.8 mm). While Shodex standard P-82 was used as a standard sample, 100 μL of 0.1M phosphate buffered saline (pH 7.4) was injected at a rate of 1 mL/min. Absorbance was measured at 280 nm. In addition, the hyaluronic acid deacetylase isolated from Scopulariopsis brevicaulis was identified by 10% SDS-PAGE. Further, isoelectric focusing was performed in a 2-D electrophoresis system using an 18-cm broad range IPG strip (pH 3-10) to examine the pI of the hyaluronic acid deacetylase.

Figure 3:
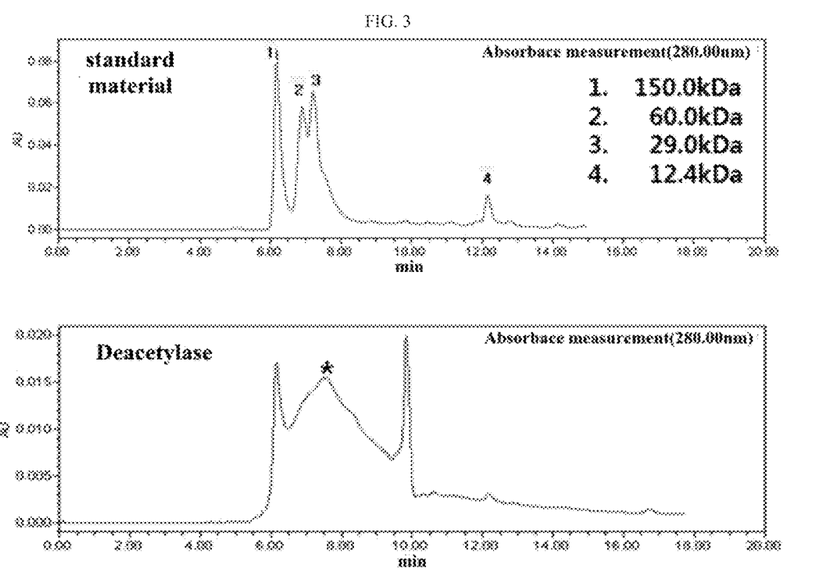
FIG. 3 shows aqueous HPLC chromatograms of a deacetylase isolated and purified from *Scopulariopsis brevicaulis*.
Figure 4:
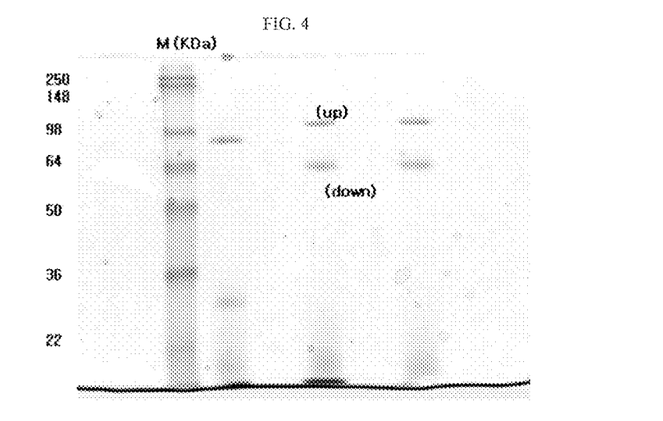
FIG. 4 is a photograph showing the isolation of a deacetylase from *Scopulariopsis brevicaulis* as analyzed by SDS-PAGE.

Analysis results of the deacetylase isolated from Scopulariopsis brevicaulis by aqueous chromatography (HPLC) and SDS-PAGE are given in FIGS. 3 and 4, respectively. The pI value of the enzyme, measured by a 2-D electrophoresis system, is given in FIG. 5.

As can be seen in FIGS. 3 and 4, the deacetylase isolated from *Scopulariopsis brevicaulis* was found to have a mean molecular weight of about 55 kDa as measured by aqueous chromatography (HPLC). This result was coincident with that of the 10% SDS-PAGE.

Figure 5:
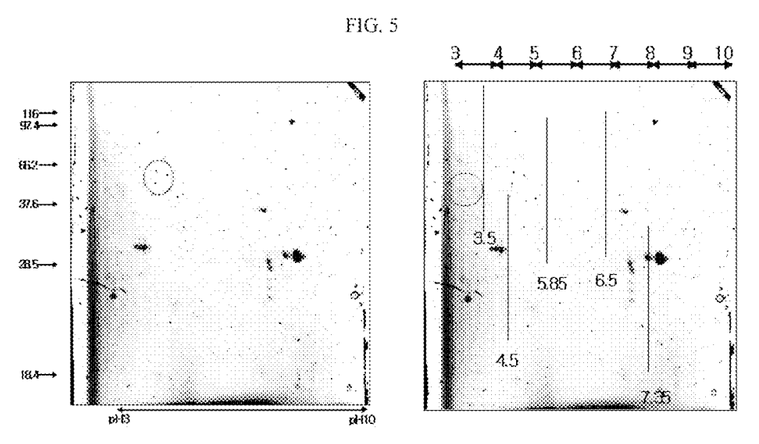
FIG. 5 shows pI values of the deacetylase isolated and purified from *Scopulariopsis brevicaulis* as analyzed by a 2-D electrophoresis system.

In addition, the deacetylase isolated from *Scopulariopsis brevicaulis* had a pI of 3.0-3.5, as shown in FIG. 5.

EXPERIMENTAL EXAMPLE 1

Comparison of Reactivity of Hyaluronic Acid Deacetylase

In each 1.5 mL e-tube were placed 50 μL of the hyaluronic acid deacetylase isolated and purified in Example 2, together with 20 μL of 10 mM hyaluronic acid (Fluka, #53747, Mw 1,400 kDa), and buffer with different pH values (pH 5.5, pH 7, pH 8.5) was added to a total volume of 200 μL. After 4 hrs of incubation, the degree of deacetylation was examined according to pH and reaction temperature (room temperature, 40° C., and 60° C.)

For a control, 330 μL of the TEA solution, 67 μL of the ATP/CoA/NAD solution, 4 μL of the MDH/CS solution, and 7 μL of the ACS solution, all contained in the acetic acid kit, were sequentially added into a 1.5 mL e-tube in the order, and each tube was filled with distilled water to a total volume of 1 mL. After reaction at 25° C. for 30 min, the reaction mixtures were transferred into 96-well plates, and absorbance at 340 nm was read on a microplate reader (SpectraMax® M2, Molecular Devices, USA). Using sodium acetate as a standard sample, a calibration curve was constructed and used to determine the levels of free acetate produced.

The activity of the hyaluronic acid deacetylase according to reaction conditions (pH, temperature) is summarized in Table 2, below.

TABLE 2

| Temp. (° C.) | pH | | |
|---|---|---|---|
| | 5.5 | 7 | 8.5 |
| Room Temp. | 3.8% | 5.8% | 6.5% |
| 40° C. | 7.5% | 10.6% | 10.8% |
| 60° C. | 12.6% | 11.8% | 20.1% |

As is well understood from the data of Table 2, the enzymatic activity of the microbial hyaluronic deacetylase increased with an increase in temperature under a weak alkaline pH condition.

EXAMPLE 3

Preparation of Deacetylated Hyaluronic Acid

To a solution of 27.5 mL (0.1 g) of hyaluronic acid (0.363%) in 55 mL of 0.1 M Tris-HCl buffer (pH 8.5) were added 68.75 mL of the hyaluronic acid deacetylase of Example 1, and then 96.25 mL of distilled water and 27.5 mL of 1M KCl. A total volume of 275 mL of the mixture was reacted at 40° C. for 4 hrs, and then mixed with at a ratio of 1:4 with 99% ethanol (Merck, #1.00983.1011) to precipitate deacetylated hyaluronic acid. The precipitate was rinsed with 99% ethanol, dissolved in distilled water, and dialyzed against distilled water. After 24 hrs of dialysis, the dialysate was lyophilized to afford deacetylated hyaluronic acid as a powder.

EXAMPLE 4

Preparation of Deacetylated Hyaluronic Acid

The hyaluronic acid deacetylase prepared in Example 2 was added in a concentration of 100 μL/mL to a 0.3% hyaluronic acid (Fluka, #53747, Mw 1,400 kDa) solution in 50 mM Tris-HCl buffer (pH 7.5), and incubated in a 55° C. water bath for 3 hrs, followed by heating at 100° C. for 2 min on a heating plate. The reaction mixture was mixed with at a ratio of 1:5 with % ethanol (Merck, #1.00983.1011) to precipitate deacetylated hyaluronic acid. The precipitate was rinsed with 99% ethanol, dissolved in distilled water, and dialyzed against distilled water. After 24 hrs of dialysis, the dialysate was lyophilized to afford deacetylated hyaluronic acid as a powder.

COMPARATIVE EXAMPLE 1

Preparation of Chemically Deacetylated Hyaluronic Acid

To 6 mL of hydrazine monohydrate was added 0.12 g of hyaluronic acid. The resulting 2% (w/v) mixture was mixed with 0.06 g of hydrazine sulfate, and reacted at 55° C. for 72 hrs with shaking. After completion of the reaction, 10 mL of chilled ethanol was added to the reaction mixture to give a precipitate. This precipitate was washed many times with ethanol, and dried in vacuo for 24 hrs. The dried sample was dissolved in 2 mL of a 5% acetic acid solution, mixed with 1.2 mL of aqueous 0.5 M iodoic acid ($HIO_3$), and left at 4° C. for 1 hr or longer. Then, 0.35 mL of aqueous 57% HI was added to the reaction solution which was subsequently vigorously stirred to give a dark violet solution. The resulting solution was placed, together with 3 mL of ethyl acetate, in a separatory funnel, and vigorously shaken for several minutes, followed by recovering the aqueous layer. This separation procedure was repeated until the color of the aqueous layer completely disappeared. The pool of the recovered aqueous layers was adjusted into a pH of 7.0~7.5 with 0.2M NaOH. The addition of ethanol formed a precipitate which was then dissolved in distilled water and dialyzed against distilled water. Lyophilization afforded the chemically deacetylated hyaluronic acid as a powder.

EXPERIMENTAL EXAMPLE 2

Measurement of Degree of Deacetylated Hyaluronic Acid

The degree of deacetylation of the deacetylated hyaluronic acid was determined by a colorimetric method in which a calibration curve for quantitating free amine with TNBS was constructed using N-acetyl-D-glucosamine as a standard sample. In detail, 2~4 mg of the deacetylated hyaluronic acid prepared in each of Examples 3 and 4 and Comparative Example 1 was dissolved in 1.0 mL of a 4% $NaHCO_3$ solution (pH 9.0) and mixed with 1.0 mL of 0.05% TNBS (2,4,6-trinitrobenzenesulfonic acid). After reacting at 40° C. for 2 hrs, 3.0 mL of 6 M HCl was added. A reaction was allowed to proceed at 60° C. for 90 min, after which the reaction mixture was sufficiently left at room temperature and then mixed with 5 mL of distilled water. Absorbance at 345 nm was measured to determine free amine levels.

The result is summarized in Table 3, below.

TABLE 3

| Deacetylated Hyaluronic acid | Degree of Deacetylation |
|---|---|
| Example 3 | 4.22 |
| Example 4 | 10.6 |
| C. Example 1 | 1.43 |

As can be seen in Table 3, the degree of deacetylation of the hyaluronic acid deacetylated by deacetylase was higher than that of the chemically deacetylated hyaluronic acid. Hence, deacetylated hyaluronic acid can be prepared more efficiently using an enzymatic hydrolysis method than a chemical method.

EXPERIMENTAL EXAMPLE 3

Assay of Deacetylated Hyaluronic Acid for Biodegradability

The biodegradability of hyaluronic acid according to the degree of deacetylation was examined as follows. First, the deacetylated hyaluronic acid prepared in Example 4 was dissolved in a citrate buffer (pH 4.5), and 0.5% hyaluronic acid was mixed as fast with 2 units/mL hyaluronidase as possible. The mixture was placed on the plate of a rheometer from 1 min after which viscosity was measured for 30 min at 37° C. under a shear stress of 1 Pa·s.

Figure 6:
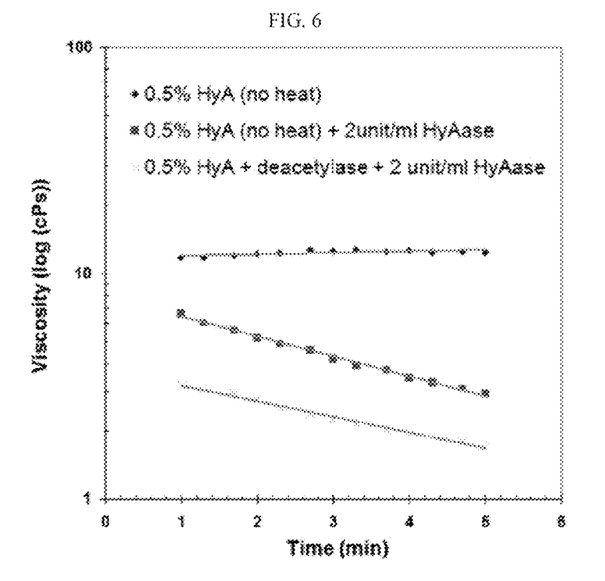
FIG. 6 is a graph showing rates of the degradation of un-deacetylated and deacetylated hyaluronic acid by hyaluronidase.

The rates at which hyaluronidase degraded deacetylated and un-deacetylated hyaluronic acid are shown in FIG. 6.

In the presence of hyaluronidase, as can be seen in FIG. 6, there is difference in the slope of viscosity against an initial period from 1 to 5 min between the deacetylated hyaluronic acid and the un-deacetylated hyaluronic acid, indicating that the initial degradation rate of the deacetylated hyaluronic acid in vivo is delayed.

EXPERIMENTAL EXAMPLE 4

Measurement of Molecular Weight of Deacetylated Hyaluronic Acid by Gel Electrophoresis Enzymatically or chemically deacetylated hyaluronic acid was examined for molecular weight by gel electrophoresis. About 2 cm-thick, 12% acrylamide gel [30% acrylamide 3.85 mL, distilled water 6.15 mL, 3% ammonium persulfate 0.5 mL, TEMED 0.01 mL] was prepared in a gel plate in a protein electrophoresis kit. Separately, a 1.2% acrylamide solution (40 mM Tris-acetate 2.425 mL, acrylamide 0.114 g, bis-acrylamide 0.006 g, 6.4% β-dimethylaminopropionitrile) was preheated to 60° C., and mixed with 0.75 mL of 3% ammonium persulfate and immediately with a 2% agarose solution. Following removal of n-butanol, the agarose-acrylamide mixture was rapidly poured onto the acrylamide gel in the gel plate and well formers were inserted. The gel was completely solidified at about 4~8° C. Un-deacetylated hyaluronic acid or the deacetylated hyaluronic acid prepared in Example 4 or Comparative Example 1 was dissolved at a concentration of 1 mg/mL in 40 mM Tris-acetate buffer (pH 6.8), mixed at a ratio of 1:4 (v/v) with a staining solution (20% sucrose, 0.001% bromophenol), and loaded in an amount of 20 μL per well with the aid of a Hamilton syringe. Electrophoresis was performed at 60 V which was elevated to 120 V when the staining solution entered the gel. Following electrophoresis, the gel was carefully separated from the gel plate and stained with a staining reagent prepared by dissolving 200 mg of toluidine blue in 100 mL of 0.1 M acetic acid. After 20 min, the gel was desalted for 90 min in 3% acetic acid (v/v) and washed with water.

Figure 7:
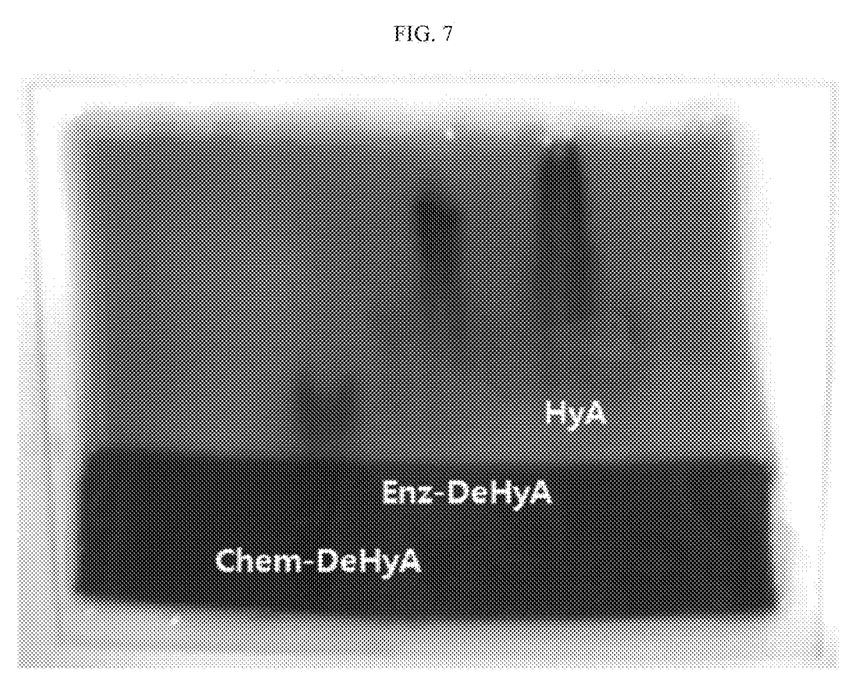
FIG. 7 is a photograph showing molecular weights of enzymatically and chemically deacetylated hyaluronic acids as measured by gel electrophoresis.

The result is given in FIG. 7.

As can be seen in FIG. 7, the enzymatically deacetylated hyaluronic acid (Example 4) was less reduced in molecular weight by hyaluronidase than was the chemically deacetylated hyaluronic acid (Comparative Example 1), indicating that the hyaluronic acid treated by deacetylase can retain a high molecular weight in vivo.

EXPERIMENTAL EXAMPLE 5

Change in Viscosity of Hyaluronic Acid with Deacetylation

Enzymatically or chemically deacetylated hyaluronic acid was examined for viscosity as follows. First, the enzymatically deacetylated hyaluronic acid (EnHyA) prepared in Example 4, the chemically deacetylated hyaluronic acid (Chem-HyA) prepared in Comparative Example 1, and un-deacetylated hyaluronic acid (HyA) were respectively dissolved in distilled water to give 0.3% solutions which were transferred onto a rheometer plate. Viscosity was measured at 37° C. under a shear stress of 1 Pa·s.

Figure 8:
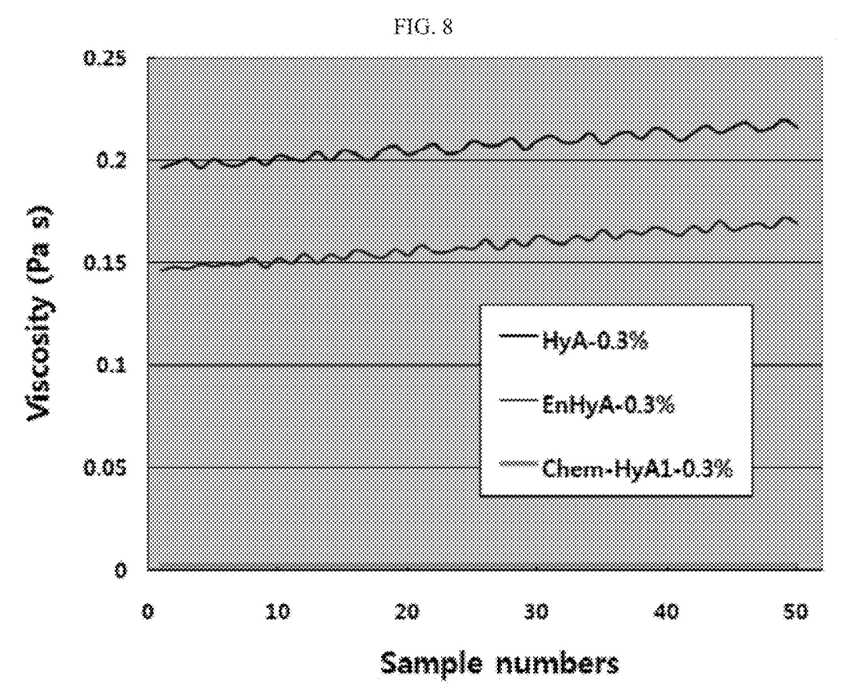
FIG. 8 is a rheogram showing the viscosity of enzymatically and chemically deacetylated hyaluronic acids.

The results are depicted in FIG. 8.

As is understood from the rheogram of FIG. 8, the enzymatically deacetylated hyaluronic acid (Example 4) was significantly less reduced in viscosity than was the chemically deacetylated hyaluronic acid (Comparative Example 1), indicating that deacetylated hyaluronic acid with high viscosity can be prepared using deacetylase.

EXPERIMENTAL EXAMPLE 6

Measurement of the Viscoelasticity Attributed to Interaction between Deacetylated Hyaluronic Acid and Beta-Glycosidylphosphate Deacetylated hyaluronic acid with cationic free amine groups was mixed with anionic beta-glycidylphosphate and the viscoelasticity of the mixture was measured according to temperature to compare gelation according to deacetylation, thereby determining the applicability of the deacetylated hyaluronic acid to hydrogel. In this regard, an aqueous 45% beta-glycidylphosphate solution was well mixed at a ratio of 1:1 (v/v) with an aqueous solution containing 0.7% un-deacetylated hyaluronic acid or deacetylated hyaluronic acid prepared in Example 4. The experiment was carried out at 4° C. in order to prevent the degradation of the un-deacetylated or deacetylated hyaluronic acid during the formation of the aqueous solution and to minimize the gelation which might occur during the mixing with the aqueous beta-glycidylphosphate solution. The mixed solution was transferred onto a rheometer plate and measured for viscoelasticity while the temperature was elevated at a rate of 1° C. per min at a frequency of 1 Hz in an oscillation mode under a shear stress of 10 Pa·s. The gel point is the temperature at which the elasticity modulus exceeds the viscous modulus.

Figure 9:
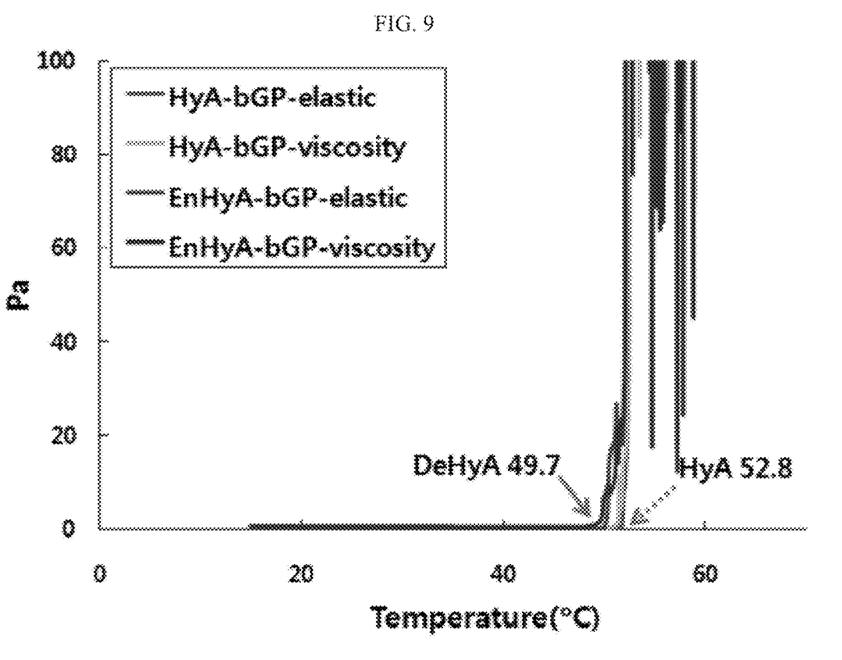
FIG. 9 is a view showing the viscoelasticity of enzymatically and chemically deacetylated hyaluronic acid according to interaction with beta-glycidylphosphate.

The results are depicted in FIG. 9.

As can be seen in FIG. 9, the gel point of the deacetylated hyaluronic acid was measured to be about 49.7° C. which was reduced by about 3.1° C. than that of the un-deacetylated hyaluronic acid, detected at about 52.8° C., indicating that deacetylated hyaluronic acid with cationic free amine groups is more apt to undergo gelation by electrostatic interaction with anionic beta-glycidylphosphate. Therefore, the deacetylated hyaluronic acid of the present invention can be applied as a carrier for cells, genes, and drugs, or a tissue engineering scaffold.

EXPERIMENTAL EXAMPLE 7

Influence of Deacetylated Hyaluronic Acid on Gelation of Chitosan/Beta-Glycidylphosphate In Experimental Example 6, the gelation of deacetylated hyaluronic acid was observed to be accelerated by electrostatic interaction with beta-glycidylphosphate. Thus, the following experiment was carried out to examine the effect of the deacetylated hyaluronic acid on the gelation of chitosan, which is known to be gelled by interaction with beta-glycidylphosphate.

An aqueous 45% beta-glycidylphosphate solution was well mixed at a ratio of 0.4:1 (v/v) with an aqueous solution containing 2.0% chitosan (degree of deacetylation 80%, Mw 700 kD, Fluka) or 2.0% the deacetylated hyaluronic acid prepared in Example 4 in distilled water, and examined for viscoelastic behavior using a rheometer. In this regard, the reaction mixture was kept at 4° C. during experiment in order to minimize the gelation which might occur during the mixing with the beta-glycidylphosphate solution. The mixed solution was transferred onto a rheometer plate and examined for viscoelasticity while the temperature was elevated at a rate of 1° C. per min at a frequency of 1 Hz in an oscillation mode under a shear stress of 10 Pa·s.

Figure 10:
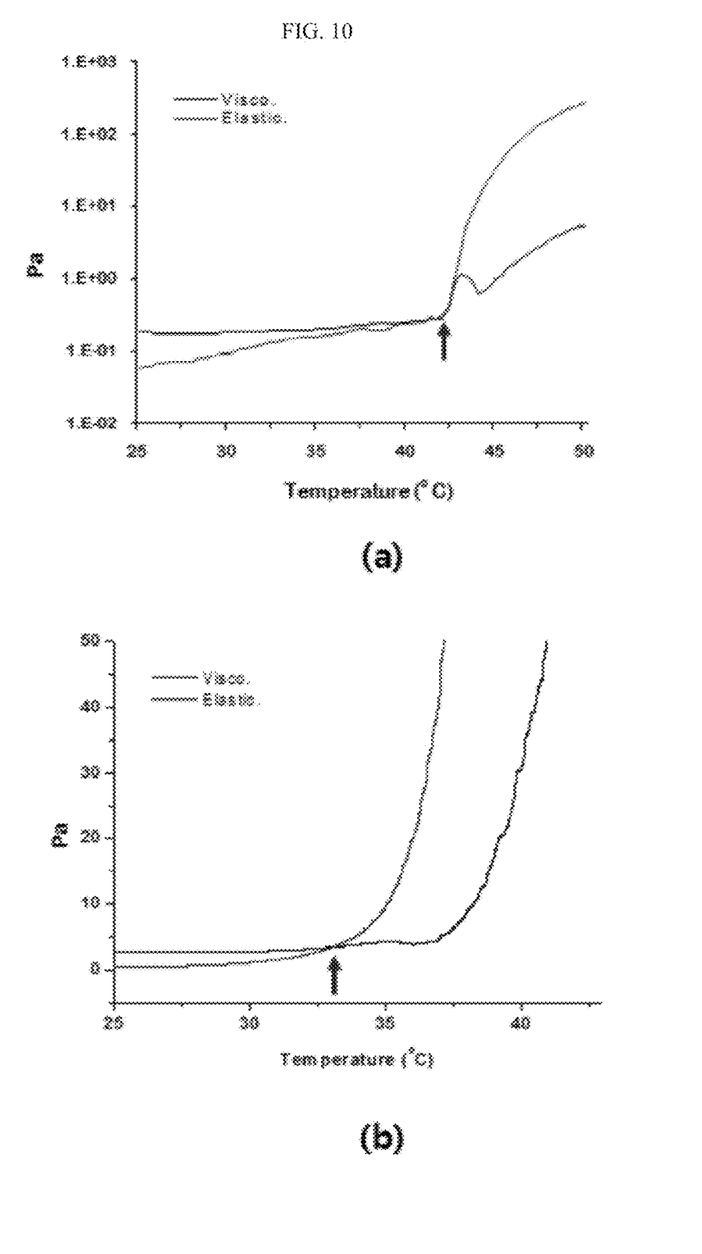
FIG. 10 shows the influence of deacetylated hyaluronic acid on the gelation of chitosan/beta-glycidylphosphate [(a) deacetylated hyaluronic acid absent, (b) deacetylated hyaluronic acid present].

The results are given in FIG. 10.

As can be seen in FIG. 10, gelation took place around 42.2° C. in the absence of the deacetylated hyaluronic acid (a), and around 33.1° C. in the presence of the deacetylated hyaluronic acid of the present invention (b). Therefore, the deacetylated hyaluronic acid of the present invention accelerated the gelation of chitosan.

EXPERIMENTAL EXAMPLE 8

Cytocompatibility of Deacetylated Hyaluronic Acid

The deacetylated hyaluronic acid of the present invention was analyzed for cytocompatibility as follows.

Human mesenchymal stromal cells (hMSCs; bone marrow derived, Lonza Walkersville, Inc., P=5) were seeded at a density of $3 \times 10^3$ cells/100 μL/well into 96-well plates, each well containing 50 μL of the MSCGM Bullet Kit medium (Catalog No: PT-3001, Lonza, Walkersville, Md. USA) and incubated at 37° C. under a relative moisture of 95% in a 5% $CO_2$ incubator to allow the cells to adhere to the scaffold. After 24 hrs of incubation, a solution containing un-deacetylated hyaluronic acid or the deacetylated hyaluronic acid prepared in Example 4 in a concentration of 0.3%, 0.6%, or 0.9% was added to each well. The cells were cultured while the culture medium was replaced every two days with a fresh medium containing the same concentration of hyaluronic acid. After 3 and 6 days of culturing, the media were removed from each well, and 500 μL of a mixture of cell counting kit-8 dye [(2-(2-methoxy-4-nitrophenyl)-3-(4-nitrophenyl)-5-(2, 4-disulfophenyl)-2H-tetrazolium, monosodium salt), DOJINDO, JAPAN] and the medium (1:9 v/v) was plated into each well, followed by incubation at 37° C. for 3 hrs in a 5% $CO_2$ incubator.

The cell culture which appeared orange due to the cell counting kit-8 dye was plated in an amount of 100 μL/well into 96-well plates before measuring absorbance at 405 nm on a microplate ELISA reader (Molecular Devices, USA) to analyze the proliferation of hMSCs according to hyaluronic acid concentration and incubation time (n=4). Cell viability was calculated from the following Mathematic Formula 1. The morphological changes of hMSCs according to the concentration of the un-deacetylated or acetylated hyaluronic acid were monitored under a microscope.

Cell Viability(%)=[Absorbance of Sample/Absorbance of Control]×100          [Mathematic Formula 1]

Figure 11:
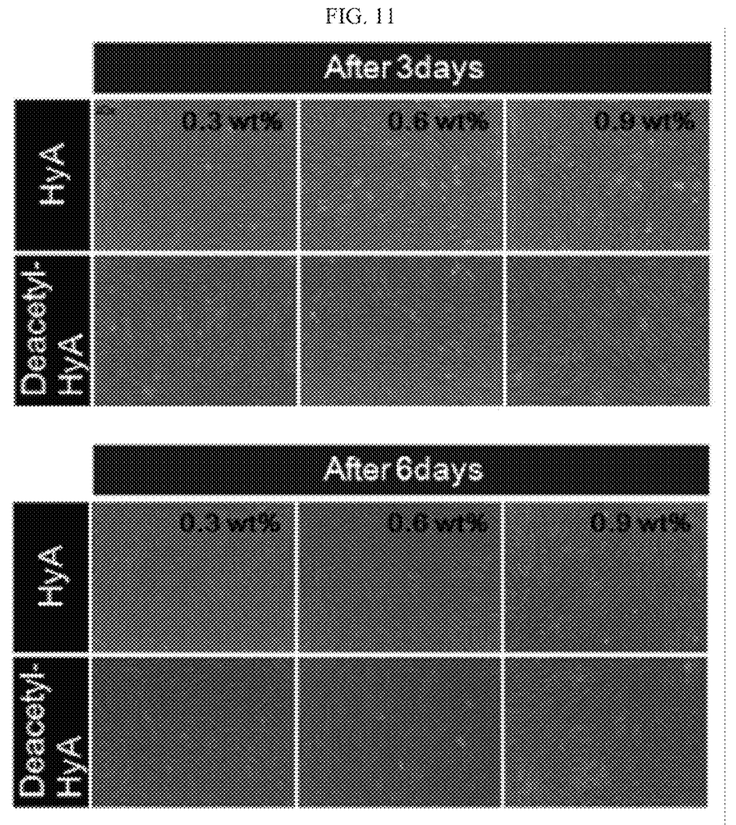
FIG. 11 shows microscopic images of hMSCs showing morphological changes with concentrations of the un-deacetylated hyaluronic acid and the acetylated hyaluronic acid.

Microscopic images showing the morphologies of hMSCs according to the concentration the un-deacetylated hyaluronic acid and the deacetylated hyaluronic acid are given in FIG. 11. Proliferation of hMSCs according to the concentration of un-deacetylated or acetylated hyaluronic acid and the time period of incubation is shown in FIG. 12.

As can be seen in FIG. 11, there was no significant difference in the morphology of hMSCs between deacetylated and un-deacetylated hyaluronic acids (24-well plate, P=5, 1.8× $10^4$ cells/mL/well), indicating that the deacetylated hyaluronic acid is cytocompatible.

Figure 12:
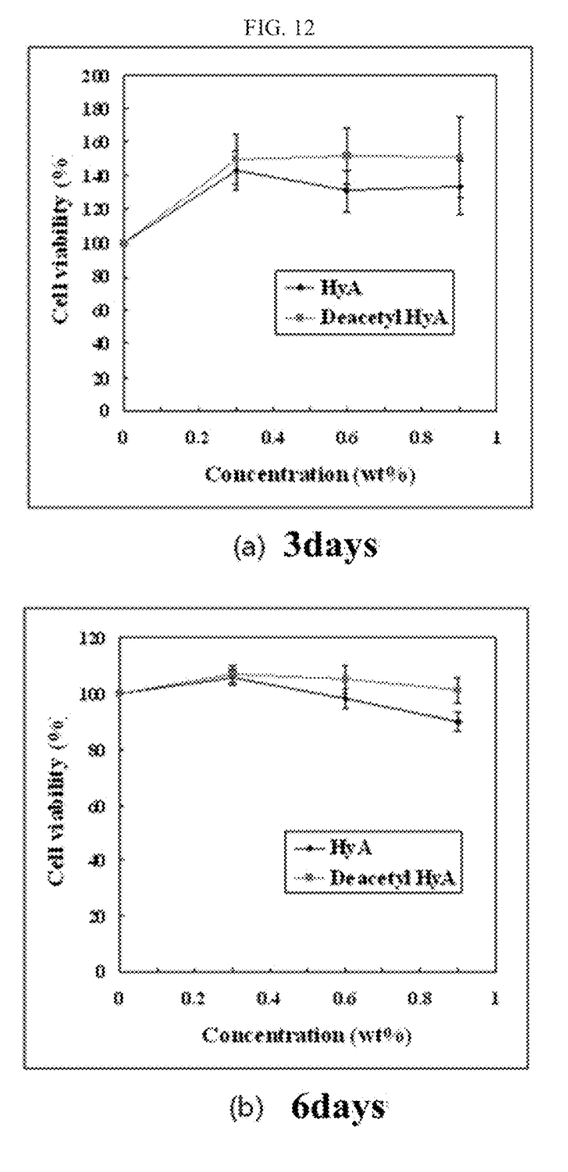
FIG. 12 shows cell viability of hMSCs according to the concentration of un-deacetylated and acetylated hyaluronic acids and the time period of incubation.

In addition, the cell viability of hMSCs decreased with an increase in the concentration of un-deacetylated hyaluronic acid, as shown in FIG. 12, which is coincident with the experiment results of Taichi Ito et al. illustrating that mesothelial cells are less apt to survive a higher concentration of hyaluronic acid and its chemical equivalent (Ito T, Fraser I P, Yeo Y, Highley C B, Bellas E, Kohane D S., Anti-inflammatory function of an in situ cross-linkable conjugate hydrogel of hyaluronic acid and dexamethasone. Biomaterials. 2007 April; 28(10):1778-86). However, the deacetylated hyaluronic acid of the present invention was found to have almost no negative influences on the cell viability of hMSCs. Therefore, the deacetylated hyaluronic acid of the present invention can be useful as a biomaterial.

Industrial Applicability

As described above, the deacetylated hyaluronic acid and its derivatives in accordance with the present invention can be usefully applied as biomaterials such as carriers for cells, genes, and drugs, or tissue engineering scaffolds.

Sequence Free Text

```
                                                  SEQ. ID. NO: 1
atgctgtttc ctaatgtgcc gggtgtggca tctcttctct cactcttcgc cgcaaccctc atcctaaaca ctcaagccct agccatcaat acaatagcaa acctcacaga ccgacaaccg cgtgtttcct acggtctata cattcaccat tgctacgttc ctggagtggt agccctaacc ttcgatgacg gaccctacat ttacacagaa gaactcctcg acatactcgc gcagtacggc gccaaagcga ccttctttgt gaatggccac aatctagctg gcaacgaatg gctcatccag cgtgttgtaa atgaaggcca ccagctagca tcgcacacat ggggccatac cgatcttact gttctcagct atgatcaaat cgtcgaccaa atgacccgac tcgagtctgc ctttgtagca tccgtcgggg tagtccctac ctacatgagg ccaccgtacc tcgccgccaa tgactatgtt ctgggcgtca tggctgaact cggctaccat gtcattggtg ctagtgtcga taccaaggac tatgagaacg atcatcctga tctgattgga cgtagtgtgg ccaagtttaa ccaggagcta gatcagggag gaacgatcgt cttgtcgcat gacattcacg aacagactgt gcgaactctg acacacatca tgctggagga agtgtacgaa cgagggttgc agcctacaac tgtcggaggt tgtcttggtg acgacgcatg gtaccgttag
```

---

The invention claimed is:

1. An isolated deacetylation hydrolases isolated from *Scopulariopsis brevicaulis* or encoded by a gene having the nucleotide sequence of SEQ ID NO: 1.

2. A method of preparing a deacetylated hyaluronic acid, the method comprising:
   contacting the deacetylation hydrolase of claim 1 with hyaluronic acid.

3. The method of claim 2, wherein said contacting comprises:
   dissolving the hyaluronic acid in a solvent to provide a solution; and
   incubating the solution in the presence of the deacetylation hydrolase.

4. The method of claim 2, wherein the solvent has pH ranging 3.0 to 9.0.

5. The method of claim 2, wherein the solution is incubated at temperature of 10-70° C.

6. The method of claim 2, wherein the solution is incubated for 0.001-24 hours.

7. A composition comprising the deacetylated hyaluronic acid, prepared by the method of claim 2.

8. A carrier for delivering a cell, a gene or a drug, the carrier comprising the deacetylated hyaluronic acid composition of claim 7.

9. A tissue engineering scaffold comprising the deacetylated hyaluronic acid composition of claim 7.

10. A method of preparing the deacetylation hydrolase of claim 1, the method comprising:
    culturing, in a culture medium, a microbe selected from the group consisting of *Aspergillus nidulans, Scopulariopsis brevicaulis, Mucor rouxii, Bacillus cereus, Colletotrichum lagenarium, Rhizopus stolonifer, Absidia coerulea, Gongronella butleri, Saccharomyces cerevisiae, Encephalitozoon cuniculi, Metarhizium anisopliae, Streptococus pneumoniae, Mortierella* sp. DY-52, *Rhizopus circinans, Vibrio cholera*, and a combination thereof; and
    collecting the deacetylation hydrolase from the culture medium.

11. The method of claim 10, wherein the microbe is *Aspergillus nidulans*.

* * * * *